United States Patent [19]

Abramitis

[11] 3,946,074

[45] Mar. 23, 1976

[54] PLANT GROWTH REGULATORY AGENTS AND PROCESS

[75] Inventor: Walter W. Abramitis, Downers Grove, Ill.

[73] Assignee: Akzona Incorporated, Asheville, N.C.

[22] Filed: Oct. 21, 1974

[21] Appl. No.: 516,715

Related U.S. Application Data

[63] Continuation-in-part of Ser. No. 78,240, Oct. 5, 1970, Pat. No. 3,857,879, which is a continuation-in-part of Ser. No. 687,438, Dec. 4, 1967, abandoned.

[52] U.S. Cl....... 260/561 K; 260/561 A; 260/561 B
[51] Int. Cl.²........................................ C07C 103/14
[58] Field of Search......... 260/561 K, 561 A, 561 B

[56] References Cited

UNITED STATES PATENTS

| | | | |
|---|---|---|---|
| 2,765,337 | 10/1956 | Benneville et al. | 260/561 K |
| 3,046,102 | 7/1962 | Andress et al. | 260/501.11 |
| 3,219,666 | 11/1965 | Norman et al. | 260/561 A |
| 3,228,972 | 1/1966 | Schwartz | 260/534 |

*Primary Examiner*—C. Davis
*Attorney, Agent, or Firm*—Francis W. Young; Philip M. Pippenger

[57] ABSTRACT

Diamides and triamides of aliphatic polycarboxylic acids which may be substituted in the alkylene group by alkyl or alkenyl groups, provide growth regulants for plants and trees. Preferred are N–substituted succindiamides.

13 Claims, No Drawings

PLANT GROWTH REGULATORY AGENTS AND PROCESS

CROSS-REFERENCE TO RELATED APPLICATIONS

This application is a continuation-in-part of copending application Ser. No. 78,240, filed October 5, 1970 now U.S. Pat. No. 3,857,879, which is in turn a continuation-in-part of application Ser. No. 687,438, filed Dec. 4, 1967, now abandoned.

BACKGROUND OF THE INVENTION

It is often desirable to retard normal growth in various trees and plants to obtain dwarfed, mature trees and plants. Such dwarfing is frequently desirable for ease of harvesting desired portions of the plant, and in many species dwarfing produces an earlier maturity and increased crop yields. One previous way of obtaining desired dwarfing was to select smaller breed varieties of plants. Also, chemical sprays have been used in the past, such as tri-iodobenzoic acid, and certain quaternary ammonium chlorides and hydrazides, but these chemicals have not always proven entirely satisfactory.

It is also often desirable to stimulate plant growth which increases flower, fruit, seed set, and production.

GENERAL DESCRIPTION OF THE INVENTION

In accordance with the present invention it has been found that excellent growth regulation of plants and trees may be obtained by the application thereto of certain diamides and triamides of aliphatic dicarboxylic acids of the formula:

$$\underset{R'}{\overset{R}{\diagdown}}N-\overset{O}{\underset{\|}{C}}-X-\overset{O}{\underset{\|}{C}}-N\underset{R_5}{\overset{R_4}{\diagup}} \qquad (1)$$
$$(R_6)_n$$

wherein X is saturated alkylene having from 1 to 6 carbon atoms; R is selected from the group consisting of hydrogen and alkyl having 1 to 18 carbon atoms; R' is alkyl having 1 to 18 carbon atoms; $R_4$ is selected from the group consisting of H and an aliphatic hydrocarbon group having 1 to 18 carbon atoms; $R_5$ is an aliphatic hydrocarbon group having from 1 to 22 carbon atoms; and $R_6$ is selected from the group consisting of hydrogen, hydroxy, halogen, carboxy, carboxamide, alkyl having 1 to 18 carbon atoms, and $\Delta^2$-alkenyl having 2 to 18 carbon atoms, and $n$ is 1 or 2.

The diamides of the foregoing formula are therefore alkylene-unsubstituted, or alkyl-substituted or alkenyl-substituted derivatives of 1–6 carbon saturated aliphatic dicarboxylic acids, illustrative examples of which include malonic acid, dimethylmalonic acid, isopropylmalonic acid, n-butylmalonic acid, n-hexylmalonic acid, succinic acid, α-methylsuccinic acid, α-ethylsuccinic acid, dodecyl succinic acid, glutaric acid, β-methylglutaric acid, α-n-propylglutaric acid, adipic acid, α-ethyladipic acid, dimethyl adipic acid, α-m-hexyl adipic acid, pimelic acid, α-ethyl pimelic acid, and suberic acid.

There are also included diamides and triamides of citric acid.

R, R', $R_4$ and $R_6$ may be alkyl or aliphatic hydrocarbon groups having 1 to 18 carbon atoms, and $R_5$ may have 1 to 22 carbon atoms. These groups may be saturated, straight chain, branched chain, primary-alkyl, secondary-alkyl, or tertiary-alkyl hydrocarbon groups. Examples of such groups include methyl, ethyl, n-propyl, isopropyl, isobutyl, n-butyl, tert.-butyl, pentyl, hexyl, heptyl, octyl, nonyl, decyl, hendecyl, dodecyl, tridecyl, tetradecyl, pentadecyl, hexadecyl, heptadecyl, and octadecyl groups, and the like.

$R_6$ may also be $\Delta^2$-alkenyl having 2 to 18 carbon atoms, that is, all the alkenyl groups have the double bond in the 2-position, at a carbon atom secondary to the carbon atoms by which the alkenyl group is attached to the alkylene group. Examples of suitable alkenyl groups include ethenyl, propenyl, butenyl, pentenyl, hexenyl, heptenyl, octenyl, nonenyl, decenyl, hendecenyl, dodecenyl, tridecenyl, tetradecenyl, pentadecenyl, heptadecenyl, and octadecenyl.

$R_6$ may also include as alkyl groups, isomeric mixtures of sec-alkyl groups such as sec-alkyl ($C_7$–$C_8$), sec-alkyl ($C_9$–$C_{10}$), sec-alkyl ($C_{11}$–$C_{14}$) and sec-alkyl ($C_{15}$–$C_{20}$), some or all of which may be derived from petroleum sources.

$R_6$ may also be halogen, such as chlorine or bromine.

$R_6$ may be hydroxy and carboxy or carboxamide, in the case of citric acid.

The preferred diamides, according to the invention, are those of substituted diamides of succinic acid of the formula:

$$\underset{R'}{\overset{R}{\diagdown}}N-\overset{O}{\underset{\|}{C}}-\overset{H}{\underset{R_7}{C}}-\overset{H}{\underset{R_8}{C}}-\overset{O}{\underset{\|}{C}}-N\underset{R_5}{\overset{R_4}{\diagup}} \qquad (2)$$

wherein R, R', $R_4$, $R_5$, have the meanings given above in formula (1), $R_7$ is hydrogen, halogen, alkyl having 1 to 18 carbon atoms, or $\Delta^2$-alkenyl having 2 to 18 carbon atoms, and $R_8$ is hydrogen or halogen.

Where an alkenyl substituent is present, the preferred substituent is $\Delta^2$-dodecenyl, which is attached at the beta-position of the succinyl group, i.e. beta to the carboxamide group.

The following compounds are illustrative of diamide growth regulants according to the invention, but are not to be considered as limiting the invention thereto:

Bis (1-methyloctyl)-beta-$\Delta^2$-dodecenyl succindiamide

Bis (1-methyldecyl)-beta-$\Delta^2$-dodecenyl succindiamide

Bis (1-methyldodecyl)-beta-$\Delta^2$-dodecenyl succindiamide

N,N-Dimethyl-N'-1-methyloctyl-beta-$\Delta^2$-dodecenyl succindiamide

N,N-Dimethyl-N'-1-methyldecyl-beta-$\Delta^2$-dodecenyl succindiamide

Bis(N-methyl-N-dodecyl)-beta-$\Delta^2$-dodecenyl succindiamide

N-Methyl-N-dodecyl-N'-methyl-N'-dodecyl-beta-$\Delta^2$-dodecenyl succindiamide

N-Methyl-N-1-methyloctyl-N',N'-dimethyl-beta-$\Delta^2$-dodecenyl succindiamide

N,N-Dimethyl-N'-1-methyldecyl fumaric diamide

N,N'-Bis(1-methyldecyl) maleic diamide

N,N'-Bis(1-methyldecyl) citric diamide

N,N'-Dipropyl-1-methyldecyl succindiamide

Bis-(1-methyldodecyl)-2,3-dibromo succindiamide

Bis-(N-methyl-N-dodecyl)-2,3-dibromo succindiamide

N,N-Dimethyl-N'-1-methyldecyl-malediamide (maleic acid)

N,N-Dimethyl-N'-methyldecyl maldiamide (malic acid)

N,N-Dimethyl-N'-1methyldecyl malondiamide (malonic acid)

N,N-Dimethyl-N'-1-methyldecyl citric diamide

N,N,N',N'-Tetramethyl-N''-1-methyldecyl citric triamide

Depending upon the amount of the compound applied and the time of the plant life cycle, the regulatory effect may be stimulation or dwarfing.

The diamides and triamides of the invention may be prepared by reacting a polycarboxylic acid of the formula

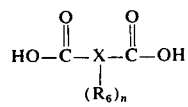

wherein X and $R_6$ have the meanings given for formula (1), or the corresponding acid-amide with a primary or secondary amine having the formula

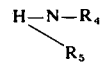

wherein $R_4$ and $R_5$ have the meanings given for formula (1), under a nitrogen blanket at a temperature of from about 105°C to about 150°C with stirring until the water formed in the reaction is given off. It will be seen that one active acid group may be reacted with one amine and another acid group with another amine, thus producing unsymmetrical di- and triamides.

It has been found that the compounds of the present invention are active plant growth regulators, and are especially effective when applied to plants and trees to obtain retardation or stimulation of growth. This activity is surprising in view of the fact that when about 5000 ppm of such known compounds as succinic acid, dodecenylsuccinic acid, dimethyl-cocoammonium dodecenyl succinate, N,N-dimethyl-beta-dodecenyl succinamic acid and N-methyl-N-dodecyl-beta-dodecenylsuccinamic acid were sprayed, in aqueous emulsions, on young tomato, snap bean, English broad bean, cotton and tobacco plants, no marked dwarfing was observed about four weeks after application.

DESCRIPTION OF THE PREFERRED EMBODIMENTS

The following example will illustrate the preparation of the compounds of the invention, but is not to be regarded as limiting:

EXAMPLE 1

Two moles of methyl dodecyl amine were mixed with $\Delta^2$-dodecenyl succinic acid and heated under a nitrogen blanket at a temperature of about 130°C with stirring until about 2 moles of water of reaction were collected. The product was bis(N-methyl, N-dodecyl)-beta-$\Delta^2$-dodecenyl succindiamide, which was a light amber liquid exhibiting moderate viscosity at 75°F, substantially insoluble in water, and soluble in the organic solvents acetone and ispropanol.

Proceeding as in Example 1, the following diamides and triamides were prepared, and exhibited the properties set forth in Table 1:

Table 1

| Product | Color | (Diamides) Viscosity 75°C | Solubility in Water | Solubility in Oil | Solubility Organic Solvent |
|---|---|---|---|---|---|
| N,N-dimethyl-N'-1-methyloctyl beta-$\Delta^2$-dodecenyl succindiamide | Amber | Moderate | Dispersable | — | Soluble |
| N,N-dimethyl-N'-1-methyldecyl beta-$\Delta^2$-dodecenyl succindiamide | Amber | Moderate | Substantially Insoluble | — | Soluble |
| Bis(1-methyloctyl)-beta-$\Delta^2$-dodecenyl succindiamide | Amber | Heavy | Substantially Insoluble | Substantially Insoluble | Soluble |
| Bis(1-methyldodecyl)-beta-$\Delta^2$-dodecenyl succindiamide | Amber | Heavy | Substantially Insoluble | — | Soluble |
| N,N-dimethyl-N'-methyldecyl-malediamide (maleic acid) | Amber | Moderate | Substantially Insoluble | — | Soluble |
| N,N-dimethyl-N'-methyldecyl maldiamide (malic acid) | Amber Light | Moderate | Substantially Insoluble | — | Soluble |
| N,N-dimethyl-N'-methyldecyl malondiamide (malonic acid) | Amber Dark | Moderate | Soluble | — | Soluble |
| N,N-dimethyl-N'-1-methyldecyl citric diamide | Amber | Moderate | Slightly Soluble | — | Soluble |
| N,N,N',N'-tetramethyl-N''-1-methyldecyl citric triamide | Amber | Heavy | Soluble | — | Soluble |

The following examples illustrate the practice of the invention in the application of the growth regulants to plants.

The plant response is dependent upon the plant species, the concentration of chemical and the time of application. In general, the greater the concentration of the chemical the more likely is a response of plant retardation or dwarfing. There may be a level at which no response is obtained and then below which there will be a plant stimulatory response. Dwarfing responses may generally be obtained with the higher concentration of chemicals on seedling plants. Stimulatory responses are obtained with application of chemicals at low level to young seedlings or at higher levels to the more mature plant.

Stimulatory effective amounts of the active chemical and retardancy effective amounts of the active chemical, according to the invention, may readily be determined by one skilled in the art in accordance with the effect desired on a particular species of plant by application of the active chemical in a range of amounts to the actively growing plant.

The plant growth regulator chemicals of this invention may be applied in many ways well known to the art to obtain particularly desired results. They may be applied in either oil or aqueous solutions when solubility of the active chemical permits, or as emulsions. Aqueoue emulsions may be formed using suitable emulsifiers, such as ethoxylated fatty acids, polysorbitan monolaurate, and the like at concentrations of from about 1 to 4 per cent by weight, based upon the total composition.

It is generally most satisfactory for general dwarfing effects to apply the active retardant in the early two or four leaf stage. However, applications at other periods of growth do result in specialized retardation or stimulating functions.

For example, the active retardant may be applied at flowering time to retard growth of flower bracts. It is especially effective to apply the growth retardants of this invention to fruit trees from early bud stage to late flowering stage to shorten terminal growth or to retard bud development to obtain dormancy during periods of dangerously low temperatures which would normally produce frosting and crop damage. In certain crops, such as soybeans, application of the chemical at flowering time does produce a stimulating or increased bean set. Another method of application of the growth regulant of the invention is to soak the plant seeds in compositions containing active chemical.

To obtain growth regulatory effects, an amount of the active chemical sufficient to obtain the desired effect should be applied in aqueous or oil solutions or emulsions. Any non-phytotoxic agricultural oil may be used. A wide range of quantities are suitable depending upon the mode of application and desired effect. Usually from about 50 to 5000 ppm is suitable for spray application. However, it is also appropriate to apply the growth retardant at a higher rate.

When applied by soaking of seeds or bublets in a solution of active chemical, concentrations of about 5 to 500 ppm are preferred. The seeds or bublets may be soaked in the active chemical for from ½ to 3 hours.

To maintain dwarfing or stimulation effects over long periods of time, it may be desirable to make multiple applications of the chemical.

The active chemicals of the invention are effective plant growth regulating agents when applied to plants generally, including wide varieties of plant life including farm crops, ornamental plants, shrubs, ornamental trees, and fruit trees.

The active chemicals of the invention may be applied in conjunction with other chemicals, such as biocides, other plant growth regulators, chemicals to aid in uptake, translocation of the chemical, and the like. Any non-interfering chemical may be applied with the chemicals of this invention.

EXAMPLE 2

Young plants were sprayed in the two to four leaf stage with a solution of N-methyl-N-dodecyl-N'-methyl N'-dodecyl beta-$\Delta^2$-dodecenyl succindiamide and the plant response and phytotoxicity observed four weeks after spraying is noted in Table 2.

Table 2

| PLANT | CONC.(PPM) | PHYTOTOXICITY | PLANT RESPONSE |
|---|---|---|---|
| Tomato | 5000 | moderate | Dwarfed |
|  | 1000 | None | Dwarfed |
| Tobacco | 5000 | Slight | Dwarfed |
|  | 1000 | None | No effect |
| Green bean | 2500 | Slight | Dwarfed |
| Cotton | 5000 | Light | Dwarfed |
| Broad bean | 5000 | Light | Dwarfed |
|  | 2500 | Slight | Normal |
| Potato | 5000 | Slight | Dwarfed for two weeks |

EXAMPLE 3

Young green bean plants were sprayed with concentrations of 2500 ppm of the same chemical described in Example 2 and 2500 ppm of gibberellin was applied in the same spray application, 24 hours after and 24 hours prior to application of the diamide. Results are shown in Table 3.

| MODE OF APPLICATION | PHYTOTOXICITY | PLANT RESPONSE |
|---|---|---|
| Diamide and Gibberellin together | None | Gibberellin effect |
| Diamide alone followed by gibberellin 24 hrs. later | None | Held dwarf 2 weeks and Gibberellin effect occurred |
| Gibberellin alone followed by diamide | None | Drawfed for at least one month |

EXAMPLE 4

Young peanut plants were sprayed with the noted chemicals at a concentration of 5000 ppm of the active chemical. Observations four weeks past spraying showed the results noted in Table 4.

Table 4

| CHEMICAL | PHYTOTOXICITY | PLANT RESPONSE |
|---|---|---|
| N-methyl N-1-methyloctyl-N',N'-dimethyl-beta-$\Delta^2$-dodecenyl succindiamide | None | Dwarfed |

EXAMPLE 5

Potted young active growing flowers were sprayed to the point of runoff with aqueous emulsions of the noted chemicals emulsified with 2% polysorbate monolaurate, and the plant response noted in Table 5 was observed 68 days after application of the chemical.

Table 5

| PLANT | CHEMICAL | CONC.(PPM) | PLANT RESPONSE |
|---|---|---|---|
| Forget-Me-Not | Bis(1-methyloctyl)-beta-$\Delta 2$-dodecenyl |  | 25% taller than |

Table 5-continued

| PLANT | CHEMICAL | CONC.(PPM) | PLANT RESPONSE |
|---|---|---|---|
| | succindiamide | 1,000 | control |
| | | 2,500 | Approx. 25% taller than control |
| " | Bis(1-methyldecyl)-beta-$\Delta^2$-dodecenyl succindiamide | 1,000 | Same as control |
| | | 2,500 | Approx. twice as tall as control |
| Zinnia | Bis(-1-methyloctyl)-beta-$\Delta^2$-1,000 dodecenyl succindiamide | 1,000 | Slightly smaller than control |
| | | 2,500 | 25% taller than control |
| " | Bis(1-methyldecyl)-beta-$\Delta^2$-dodecenyl succindiamide | 1,000 | Same as control |
| | | 2,500 | Approx. 25% taller than control |

EXAMPLE 6

Young peanut plants, in a green house test, were sprayed to the point of runoff with aqueous emulsions of the noted chemicals emulsified with 2% polysorbate monolaurate, and the plant response noted in Table 6 was observed 59 days after application of the chemical by comparison with untreated controls.

Table 6

| CHEMICAL | CONC.(PPM) | PLANT RESPONSE |
|---|---|---|
| Bis(1-methyloctyl)-beta-$\Delta^2$-dodecenyl succindiamide | 5,000 | Approx. 25% taller than control |
| Bis(1-methyldecyl)-beta-$\Delta^2$-dodecenyl succindiamide | 5,000 | Approx. 25% taller than control |

EXAMPLE 7

Young Belladonna plants, strain No. 49, in a green house test, were sprayed to the point of runoff with aqueous emulsions of the noted chemicals emulsified with 2% polysorbate monolaurate, and the plant response noted in Table 7a was observed 28 days after application of the chemical by comparison with untreated controls.

Table 7a

| CHEMICAL | CONC.(PPM) | PLANT RESPONSE |
|---|---|---|
| Bis(1-methyloctyl)-beta-$\Delta$-dodecyl succindiamide | 5,000 | Leaves about 15 to 20% larger in area than control |
| Bis(1-methyldecyl)-beta-$\Delta^2$-dodecenyl succindiamide | 5,000 | Leaves about 40% larger in area than control |

Additional plant responses at 28 days are shown in Table 7b.

Table 7b

| Chemical | Conc. (ppm) | Main Stem cm. | Green Stem wt. gm. | Main Leaves No. | Wt.gm. | Secondary Lvs. No. | Wt.gm. | Total Green Wt.gm. |
|---|---|---|---|---|---|---|---|---|
| N,N-dimethyl-N'-1-methyldecyl -fumaric diamide | 5,000 | 49.0 | 23 | 27 | 86 | 24 | 8 | 117 |
| N,N'-bis(1-methyldecyl) maleic diamide | 5,000 | 47.0 | 20 | 28 | 76 | 8 | 1 | 97 |
| N,N'-bis(1-methyldecyl) citric diamide | 5,000 | 50.5 | 21 | 28 | 81 | 4 | 0.5 | 102 |
| No treatment | 5,000 | 42.0 | 15.0 | 27 | 69 | 12 | 8 | 92 |

EXAMPLE 8

Six Flue Tobacco seedling transplants about ½ inch tall were sprayed to the point of runoff with 5 ml. of aqueous emulsions of the noted chemicals emulsified with 2% polysorbate monolaurate, in green house tests, and the plant response noted in Table 8 was observed 113 days after application of the chemical by comparison with untreated controls.

Table 8

| CHEMICAL | CONC. (PPM) | PLANT RESPONSE |
|---|---|---|
| No treatment | — | 5.6" |
| Bis(1-methyloctyl)-beta-$\Delta^2$-dodecenyl succindiamide | 1,000 | 6.2" |
| Bis(1-methyldecyl)-beta-$\Delta^2$-dodecenyl succindiamide | 1,000 | 6.9" |

EXAMPLE 9

Young English Broad Bean plants were sprayed to the point of runoff with 1 ml. per plant of aqueous emulsions of the noted chemicals emulsified with 2% polysorbate monolaurate, in green house tests, and the plant response noted in Table 9 was observed 23 days after spraying.

Table 9

| CHEMICAL | CONC. (PPM) | PLANT RESPONSE |
| --- | --- | --- |
| Bis(1-methyloctyl)-beta-$\Delta^2$-dodecenyl succindiamide | 1,000 | Approx. 25% taller than control |
| Bis(1-methyldecyl)-beta-$\Delta^2$-dodecenyl succindiamide | 1,000 | Approx. 25% taller than control |

EXAMPLE 10

Flue tobacco plants approximately 6 to 10 inches tall were sprayed to the point of runoff with aqueoue emulsions of the noted chemicals, emulsified with 2% polysorbate monolaurate, and the seventh, 10th, and 13th leaves were harvested 73 days after spraying and the weights of the primed leaves were as noted in Table 10.

Table 10

| CHEMICAL | CONC. (PPM) | Weight in grams of leaves primed | | | |
| --- | --- | --- | --- | --- | --- |
| | | 7th | 10th | 13th | Total |
| No treatment | — | 14.0 | 17.5 | 19.9 | 51.4 |
| Bis(1-methyl-octyl)-beta-$\Delta^2$-dodecenyl succindiamide | 1,000 | 14.3 | 22.2 | 16.1 | 52.6 |
| Bis(1-methyl-beta-$\Delta^2$-dodecenyl succindiamide | 1,000 | 13.1 | 20.8 | 21.0 | 54.9 |

EXAMPLE 11

Onion sets were divided into groups of 10 onion sets each and four replicates using 40 onion sets were subjected to each of the following treatments. Aqueous solutions of the noted chemicals were prepared and the onion sets were soaked therein for a period of 30 minutes following which the onion sets were planted. The soaked onion sets were harvested 69 days after soaking and planting with the following results:

Table 11a

| CHEMICAL | CONC. (PPM) | AVERAGE WT. PER ONION IN GRAMS |
| --- | --- | --- |
| Control, water soak | — | 91.9 |
| Bis(1-methyloctyl)-beta-$\Delta^2$-dodecenyl succindiamide | 50 | 96.6 |
| Bis(1-methyloctyl)-beta-$\Delta^2$-dodecenyl succindiamide | 500 | 100.8 |
| Bis(1-methyloctyl)-beta-$\Delta^2$-dodecenyl succindiamide | 1000 | 102.2 |
| Bis(1-methyldecyl)-beta-$\Delta^2$-dodecenyl succindiamide | 50 | 107.6 |
| Bis(1-methyldecyl)-beta-$\Delta^2$-dodecenyl succindiamide | 500 | 103.9 |
| Bis(1-methyldecyl)-beta-$\Delta^2$-dodecenyl succindiamide | 1000 | 95.2 |

Non-treated onion sets were planted in soil for later spray treatment at the same time the soaked onion sets were planted. Nineteen days after planting, when the sets had foliage, random blocks of 40 onion plants each were sprayed with aqueous emulsions of the noted chemical and the response 50 days after spraying was observed as in Table 11b.

Table 11b

| CHEMICAL | CONC. (PPM) | AVERAGE WT. PER ONION IN GRAMS |
| --- | --- | --- |
| Control, no treatment | — | 51.3 |
| Bis(1-methyloctyl)-beta-$\Delta^2$-dodecenyl succindiamide | 50 | 52.1 |
| Bis(1-methyloctyl)-beta-$\Delta^2$-dodecenyl succindiamide | 500 | 56.2 |
| Bis(1-methyloctyl)-beta-$\Delta^2$-dodecenyl succindiamide | 1000 | 55.5 |

EXAMPLE 12

Soybeans in the first trifoliate stage were sprayed with aqueous solutions of the noted chemical at the rate of 0.5 pounds active chemical per acre and maintained in the greenhouse under 16 hours daylight Grow-Lux lights. The plants were observed after 102 days and showed the following results:

Table 12

| CHEMICAL | Number | | Pod & Bean Wt. in grams |
| --- | --- | --- | --- |
| | Pods | Beans | |
| Control, no treatment | 5 | 11 | 1.17 |
| N,N-dipropyl-1-methyldecyl succindiamide | 15 | 30 | 16.49 |
| Bis(N-methyl-N-dodecyl) beta-$\Delta^2$-dodecenyl succindiamide | 15 | 36 | 13.44 |
| Bis(1-methyldodecyl)-dibromo succindiamide | 16 | 32 | 9.54 |
| Bis(N-methyl-N-dodecyl) dibromo succindiamide | 13 | 26 | 7.92 |
| Bis(1-methyloctyl)-beta-$\Delta^2$-dodecenyl succindiamide | 9 | 15 | 3.09 |
| Bis(1-methyldecyl)-beta-$\Delta^2$-dodecenyl succindiamide | 10 | 17 | 2.74 |

EXAMPLE 13

Ten red Delicious apple trees, Starkimson variety, at the second leaf stage were sprayed with Bis(1-methyloctyl)-beta-$\Delta^2$-dodecenyl succindiamide at 5,000 parts per million in an aqueous emulsion in early June. One month later a slight chlorosis was noted in the treated trees. The treated trees were compared with untreated control trees five months after spraying and the following measurements were taken.

Table 13

| TREATMENT | CONC (PPM) | Averg. Trunk Dia.mm | No. lateral Branches/Tree | Spurs p/tree |
|---|---|---|---|---|
| Check, no treatment | — | 31.7 | 13.0 | 22.6 |
| Bis(1-methyloctyl)-beta-$\Delta^2$-dodecenyl succindiamide | 5,000 | 31.9 | 16.7 | 11.1 |

The above observations show good stimulatory effects in that more lateral branches were produced on the treated trees than on the untreated trees.

EXAMPLE 14

Tetrachlorothiophene has been used as a soil fumigant for the control of various nematodes prior to planting of plants. Tobacco plants have been affected by the pretreatment of soil with tetrachlorothiophene causing dwarfing and lower tobacco yield. Application of plant regulatory agents of this invention in stimulating amounts to flue tobacco plants planted in soil pretreated with tetrachlorothiophene, caused the plants to grow normally. The aqueous emulsion spray application of plant regulatory agents of this invention stimulated tobacoo growth within normal ranges, thus providing increased tobacco yields from tetrachlorothiophene treated soil wherein the tobacco plants were sprayed with the noted chemical at about 1 week after transplant.

Table 14

| Treatment | Rate/A | Growth Rating+ | Greenness Rating++ | No. of Nematodes 150 cc Soil | | Root Gall Index+++ | Yield Lb.Wt. Green Cured | |
|---|---|---|---|---|---|---|---|---|
| | | | | Total | Meloidognye | | Plot | A |
| Control (no treatment) | — | 2.3 | 2.3 | 400 | 30 | 4.3 | 24 | 1200 |
| Tetrachlorothiophene (pre-planting) | 3 lbs. | 2.7 | 2.2 | 302 | 0 | 3.1 | 24 | 1167 |
| Tetrachlorothiophene (pre-planting) | 3 lbs. | | | | | | | |
| Dodecenyl succindiamide (post-planting) | 2 lbs. | 3.2 | 3.2 | 387 | 0 | 2.9 | 30 | 1460 |
| Tetrachlorothiophene (pre-planting) | 3 lbs. | | | | | | | |
| Bis(1-methyldecyl)-dodecenyl succindiamide (post-planting) | 2 lbs. | 3.5 | 3.3 | 712 | 0 | 3.3 | 35 | 1700 |

+1 poor, 5 excellent
++1 yellow, 5 dark green
+++1 no galls, 5 maximum

EXAMPLE 15

Aqueous emulsions of Bis(1-methyloctyl)-beta-$\Delta^2$-dodecenyl succindiamide were applied in aqueous sprays at 1,500 and 3,000 ppm (1½ and 3 lbs. per acre) to greenhouse pots of wheat previously treated with various levels of nitrogen fertilizer. The spray application was made just as the seed head was differentiating about 80 days after planting. Computer analysis of the resulting data showed yield increases are highly significant and a correlation between fertilization and the application of Bis(1-methyloctyl)-beta-$\Delta^2$-dodecenyl succindiamide.

Table 15

| Lbs. Nitrogen appl/plot | YIELD, GRAMS | | | | | | | |
|---|---|---|---|---|---|---|---|---|
| | 166 Variety Wheat Chemical Applied | | | | | SC Variety Wheat Chemical Applied | | |
| | 0 | 1500 ppm | 3000 ppm | X | O | 1500 ppm | 3000 ppm | X |
| 0 | 5.0 | 5.6 | 6.4 | 5.6 | 4.5 | 4.6 | 5.8 | 5.0 |
| 1.5 | 19.2 | 19.7 | 17.6 | 18.8++ | 14.8 | 16.9 | 15.5 | 15.7++ |
| 3.0 | 20.6 | 24.0 | 23.6 | 22.7++ | 22.7 | 26.1 | 24.2 | 24.3++ |
| | | | | STEM LENGTH, MM | | | | |
| 0 | 561 | 522 | 542 | 542 | 586 | 609 | 641 | 612 |
| 1.5 | 525 | 553 | 529 | 536 | 679 | 696 | 742 | 706 |
| 3.0 | 528 | 565 | 623 | 572++ | 687 | 714 | 730 | 677 |
| | | | | SPIKE BEARING STEMS | | | | |
| 0 | 3.5 | 4.0 | 4.0 | 3.8++ | 4.2 | 4.2 | 5.0 | 4.5++ |
| 1.5 | 10.2 | 10.2 | 10.5 | 10.3++ | 12.8 | 13.8 | 13.2 | 13.2++ |
| 3.0 | 15.2 | 14.0 | 14.8 | 14.7++ | 16.2 | 18.0 | 16.8 | 17.0++ |
| | | | | SEED, NO/POT | | | | |
| 0 | 143.2 | 164.5 | 204.2 | 170.7+ | 126.5 | 145.5 | 219 | 168.8 |
| 1.5 | 483.8 | 508.2 | 530.8 | 507.6+ | 389.5 | 462.2 | 457.5 | 436.4 |
| 3.0 | 462.0 | 549.8 | 616.2 | 542.7+ | 490.0 | 644.2 | 635.0 | 589.8 |

+Significant at 1% level
++Significant at 5% level

EXAMPLE 16

Large scale plots on rice treated with Bis(1-methyldecyl)-beta-$\Delta^2$-dodecenyl succindiamide show a striking visual difference prior to harvest. These differences are shown in increased yields of the number of spike

What is claimed is:

1. A compound of the formula:

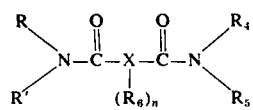

wherein X is saturated alkylene having from 1 to 6 carbon atoms; R is selected from the group consisting of hydrogen and alkyl having 1 to 18 carbon atoms; R' is alkyl having 1 to 18 carbon atoms; $R_4$ is selected from the group consisting of hydrogen and an aliphatic hydrocarbon group having 1 to 18 carbon atoms; $R_5$ is an aliphatic hydrocarbon group having 1 to 22 carbon atoms; $R_6$ is selected from the group consisting of halogen, hydroxy, carboxy, carboxamide, alkyl having 1 to 20 carbon atoms, and $\Delta^2$-alkenyl having 2 to 18 carbon atoms; and n is an integer from 1 to 2.

2. A compound of the formula:

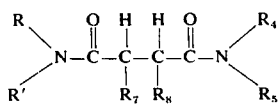

wherein R is selected from the group consisting of hydrogen and alkyl having 1 to 18 carbon atoms; R' is alkyl having 1 to 18 carbon atoms; $R_4$ is selected from the group consisting of hydrogen and an aliphatic hydrocarbon group having 1 to 18 carbon atoms; $R_5$ is an aliphatic hydrocarbon group having 1 to 22 carbon atoms; $R_7$ is selected from the group consisting of hydroxy, halogen, alkyl having 1 to 20 carbon atoms, and $\Delta^2$-alkenyl having 2 to 18 carbon atoms; and $R_8$ is selected from the group consisting of hydrogen and halogen.

3. A compound of the formula:

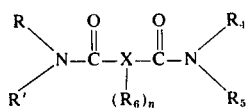

wherein X is saturated alkylene having from 1 to 6 carbon atoms; R is selected from the group consisting of hydrogen and alkyl having 1 to 18 carbon atoms; R' is alkyl having 1 to 18 carbon atoms; $R_4$ is selected from the group consisting of hydrogen and an aliphatic hydrocarbon group having 1 to 18 carbon atoms; $R_5$ is an aliphatic hydrocarbon group having 1 to 22 carbon atoms; $R_6$ is selected from the group consisting of halogen, hydroxy, carboxy, carboxamide, sec.alkyl having 7 to 20 carbon atoms, and $\Delta^2$-alkenyl having 2 to 18 carbon atoms; and n is an integer from 1 to 2.

4. Bis (1-methyloctyl)-beta-$\Delta^2$-dodecenyl succindiamide.

5. Bis (1-methyldecyl)-beta-$\Delta^2$-dodecenyl succindiamide.

6. Bis (1-methyldodecyl)-beta-$\Delta^2$-dodecenyl succindiamide.

7. N,N-Dimethyl-N'-1-methyloctyl-beta-$\Delta^2$-dodecenyl succindiamide.

8. Bis (N-methyl-N-dodecyl)-beta-$\Delta^2$-dodecenyl succindiamide.

9. N-N-Dimethyl-N'-1-methyldecyl-beta-$\Delta^2$-dodecenyl succindiamide.

10. N,N-Dimethyl-N'-1-methyldecyl citric diamide.

11. Bis-(1-methyldodecyl)-2,3-dibromo succindiamide.

12. Bis-(N-methyl-N-dodecyl)-2,3-dibromo succindiamide.

13. N,N,N',N'-Tetramethyl-N''-1-methyldecyl citric triamide.

* * * * *